United States Patent
Keltjens et al.

(10) Patent No.: US 12,410,126 B2
(45) Date of Patent: Sep. 9, 2025

(54) PROCESS FOR MAKING SIPONIMOD AND INTERMEDIATE THEREOF

(71) Applicant: Synthon B.V., Nijmegen (NL)

(72) Inventors: Rolf Keltjens, Nijmegen (NL); Ondrej Hylse, Blansko (CZ); Jiri Partl, Blansko (CZ)

(73) Assignee: Synthon B.V., Nijmegen (NL)

( * ) Notice: Subject to any disclaimer, the term of this patent is extended or adjusted under 35 U.S.C. 154(b) by 1016 days.

(21) Appl. No.: 17/599,868

(22) PCT Filed: Mar. 29, 2020

(86) PCT No.: PCT/EP2020/058884
§ 371 (c)(1),
(2) Date: Sep. 29, 2021

(87) PCT Pub. No.: WO2020/201172
PCT Pub. Date: Oct. 8, 2020

(65) Prior Publication Data
US 2022/0204446 A1   Jun. 30, 2022

(30) Foreign Application Priority Data

Mar. 29, 2019 (EP) .................................. 19166209
Dec. 16, 2019 (EP) .................................. 19216424

(51) Int. Cl.
| | | |
|---|---|---|
| C07D 205/04 | (2006.01) |
| C07C 17/16 | (2006.01) |
| C07C 17/18 | (2006.01) |
| C07C 22/08 | (2006.01) |
| C07C 249/08 | (2006.01) |
| C07C 249/12 | (2006.01) |
| C07C 251/48 | (2006.01) |
| C07C 251/52 | (2006.01) |
| C07C 303/28 | (2006.01) |
| C07C 309/66 | (2006.01) |

(52) U.S. Cl.
CPC ............ *C07D 205/04* (2013.01); *C07C 17/16* (2013.01); *C07C 249/08* (2013.01); *C07C 249/12* (2013.01); *C07C 303/28* (2013.01)

(58) Field of Classification Search
CPC ..... C07D 205/04; C07C 17/16; C07C 249/08; C07C 249/12; C07C 303/28; C07C 251/48; C07C 251/52; C07C 309/66; C07C 2601/14; C07C 22/08
See application file for complete search history.

(56) References Cited

FOREIGN PATENT DOCUMENTS

| WO | WO 2004/103306 A2 | 12/2004 |
| WO | WO 2010/071794 A1 | 6/2010 |
| WO | WO 2013/113915 A1 | 8/2013 |
| WO | WO 2017/120124 A1 | 7/2017 |

*Primary Examiner* — Sun Jae Yoo
(74) *Attorney, Agent, or Firm* — Buscher Patent PLLC

(57) ABSTRACT

The presented invention relates to a process for preparation of compound of formula (I) or a salt or a solvate thereof (i.e.) siponimod. The invention also relates to intermediates used in the process and solid forms of these intermediates.

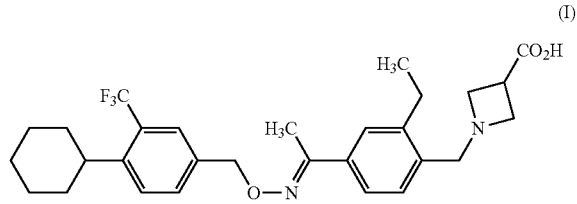

(I)

15 Claims, 4 Drawing Sheets

PROCESS FOR MAKING SIPONIMOD AND INTERMEDIATE THEREOF

BACKGROUND OF THE PRESENT INVENTION

The present invention relates to an improved process for making the compound Siponimod.

Siponimod, 1-{4-[1-(4-cyclohexyl-3-trifluoromethyl-benzyloxyimino)-ethyl]-2-ethyl-benzyl}-azetidine-3-carboxylic acid of formula (I),

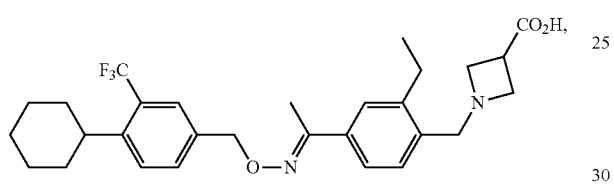

is a lysophospholipid EDG1 (S1P1) receptor ligand that is useful for treatment of immunological disorders. Fumaric acid salt of siponimod is now ongoing pre-registration for use in the treatment secondary progressive multiple sclerosis.

Siponimod was first disclosed in WO2004/103306 by Novartis. A process for preparation of Siponimod is disclosed in WO2013/113915 application. The process disclosed in WO2013/113915 application is depicted in following scheme:

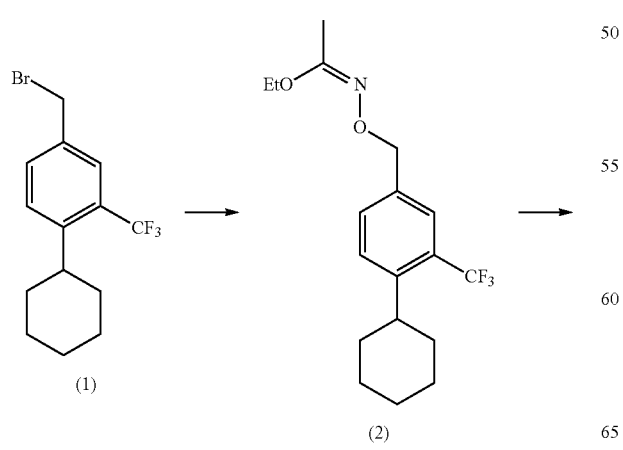

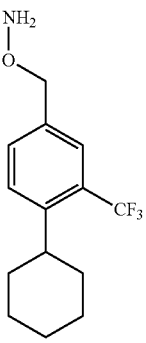

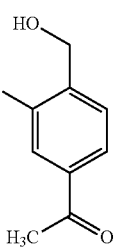

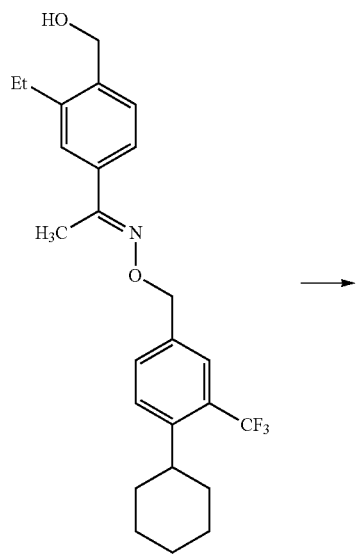

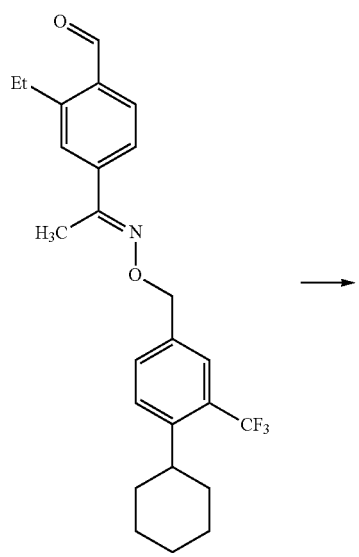

-continued

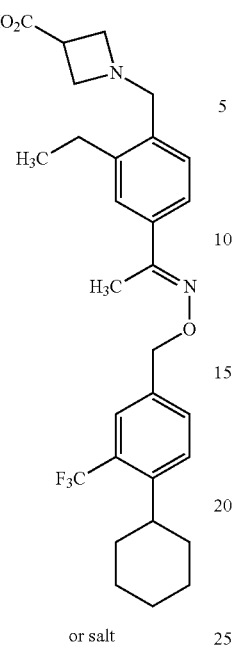

or salt

The disadvantages of the process disclosed in WO2013/113915 are:
1. The process number of reaction steps to obtain siponimod from the compound (1) is high;
2. The compounds (1) and (2) are obtained if form of oils. The possibility to purify oily compound is limited, column purification is frequently used.
Chromatographic purification steps are tedious and expensive process steps on an industrial scale;
3. The overall yield of the process (calculated from compound (1)) is low, about 26% of the theoretical yield Therefore, there is a need for alternative shorter processes that does not comprise chromatographic purification and provides siponimod in sufficient purity and yield.

SUMMARY OF THE INVENTION

The presented invention relates to a process for preparation of Siponimod of formula (I),

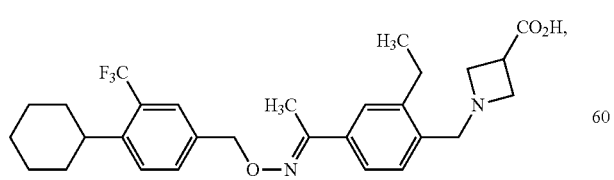

(I)

or a salt thereof or a solvate thereof, the process comprising:
a. Reacting compound of formula (II) with a compound of formula (III),

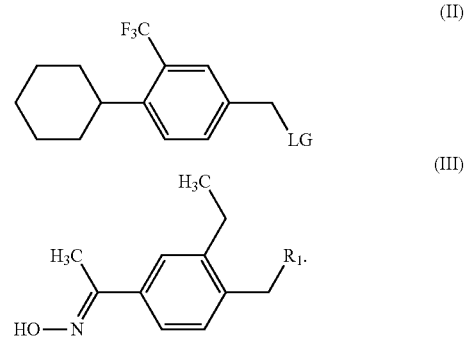

LG means a leaving group, $R_1$ means OH or OProt, Prot means hydroxyl protective group,
preferably LG is $OS(O)_2CH_3$, i.e. compound of formula (IIb) and $R_1$ is OH, i.e. compound of formula (IIIa),

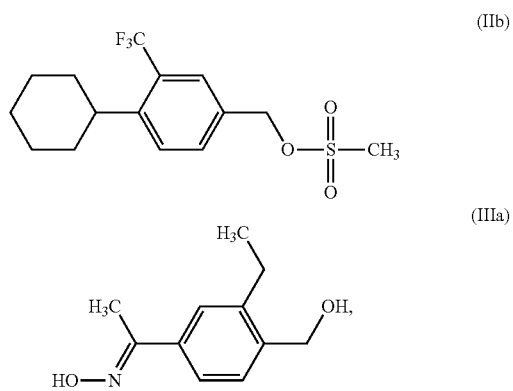

to obtain compound of formula (IV),

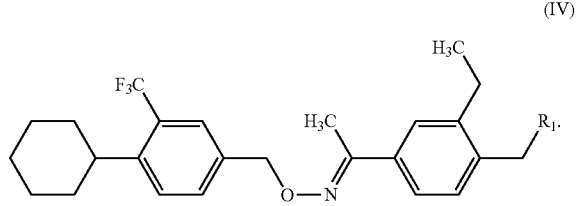

$R_1$ means OH or OProt, Prot means hydroxyl protective group,
preferably $R_1$ is OH, i.e. compound of formula (IVa) is obtained:

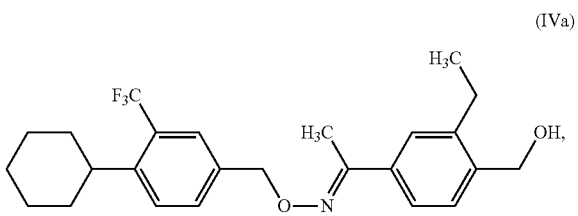 [SMILES: CCc1cc(/C(C)=N/OCc2ccc(C3CCCCC3)c(C(F)(F)F)c2)ccc1CO]

b. Transforming the compound of formula (IV) into Siponimod or a salt thereof or a solvate thereof.

The presented process further relates to the compound of formula (III),

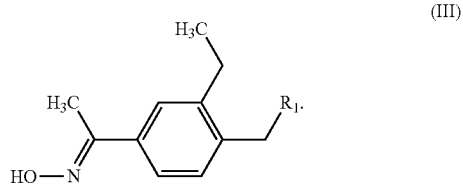

R₁ means OH or OProt, Prot means hydroxyl protective group, preferably R₁ means OH and solid forms thereof.

The presented invention further relates to solid forms of compound of formula (IIa),

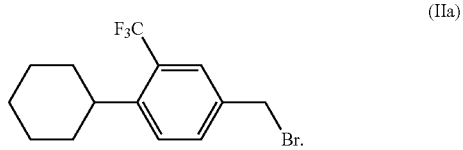 [SMILES: FC(F)(F)c1cc(CBr)ccc1C1CCCCC1]

The presented invention further relates to solid forms of compound of formula (IIb),

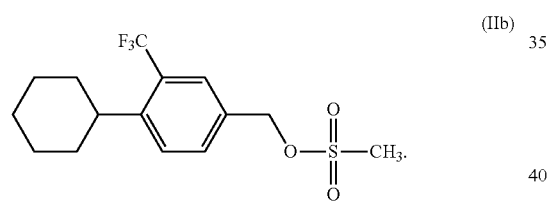

The presented invention also relates to solid forms of compound of formula (VII),

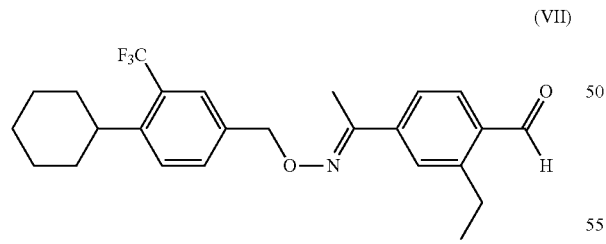

DETAILED DESCRIPTION OF THE INVENTION

Figure 1:
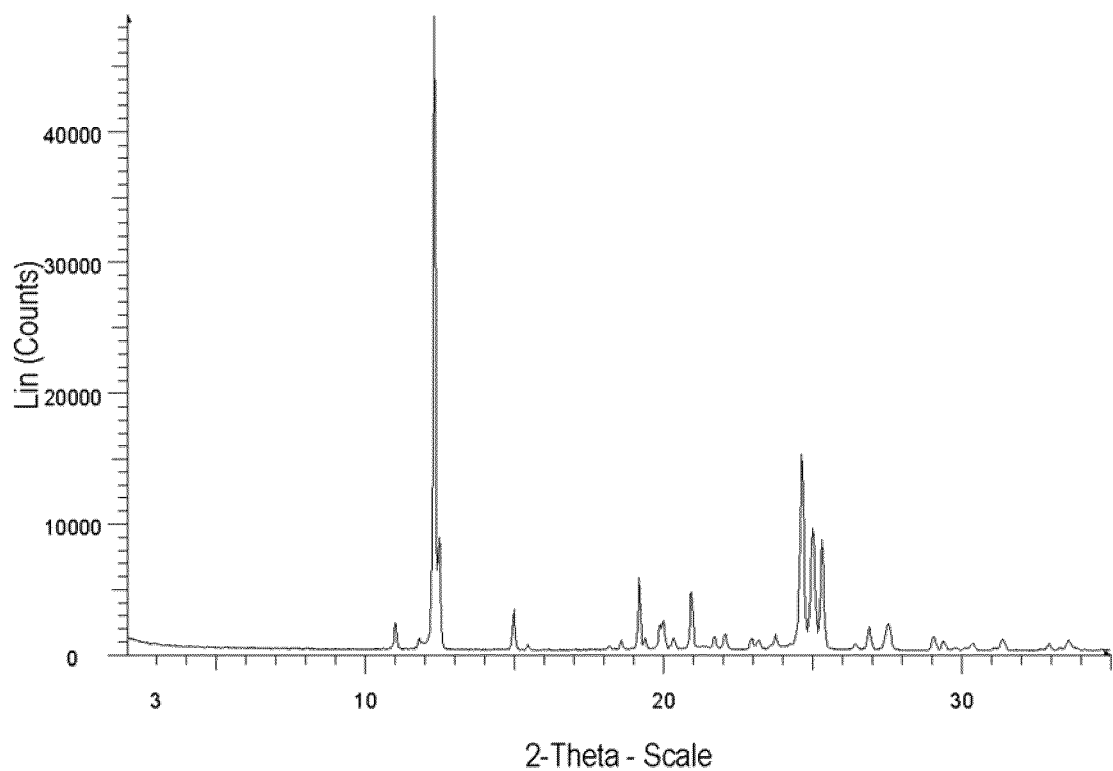
FIG. 1: XRPD pattern of the solid form of compound of formula (IIIa) prepared according to Example 2 or Example 3.

The presented invention relates to a process for preparation of Siponimod of formula (I),

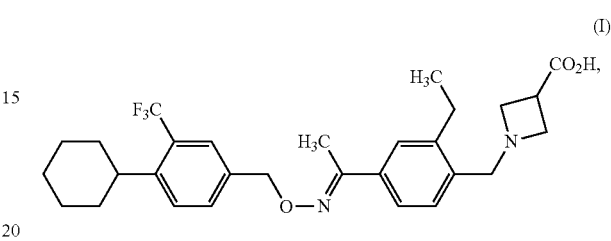

or a salt thereof or a solvate thereof, the process comprising:

a. Reacting compound of formula (II) with a compound of formula (III),

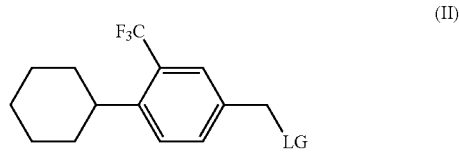

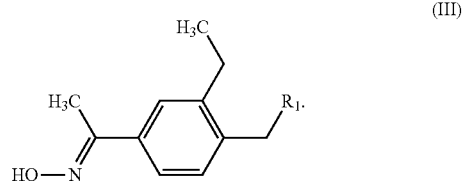

LG means a leaving group, R₁ means OH or OProt, Prot means hydroxyl protective group, to obtain compound of formula (IV),

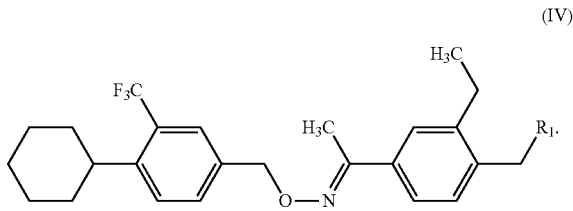

R₁ means OH or OProt, Prot means hydroxyl protective group;

b. Transforming the compound of formula (IV) into Siponimod or a salt thereof or a solvate thereof.

Presented invention also relates to a process for preparation of Siponimod of formula (I),

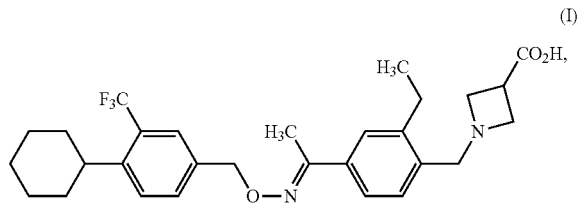 [SMILES: CCc1cc(/C(C)=N/OCc2ccc(C3CCCCC3)c(C(F)(F)F)c2)ccc1CN1CC(C(=O)O)C1]

or a salt thereof or a solvate thereof, the process comprising:
a. Reacting compound of formula (IIb) with a compound of formula (IIIa):

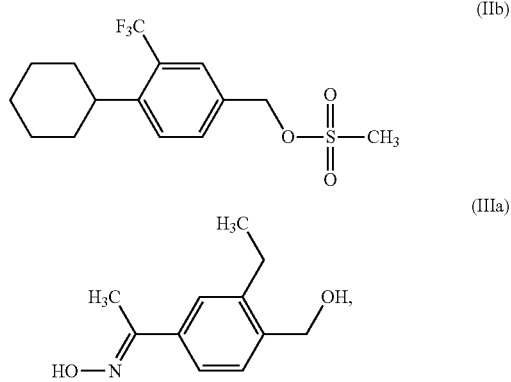

to obtain compound of formula (IVa):

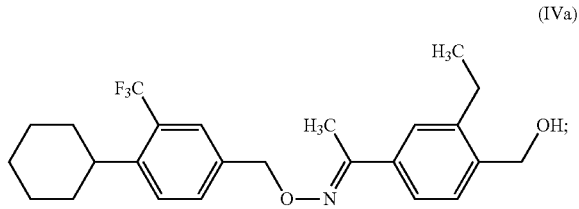 [SMILES: CCc1cc(/C(C)=N/OCc2ccc(C3CCCCC3)c(C(F)(F)F)c2)ccc1CO]

b. Transforming the compound of formula (IVa) into Siponimod or a salt thereof or a solvate thereof.

LG in compound of formula (II) means a suitable leaving group such as a halogen (such as Cl or Br or I) or $C_1$-$C_{10}$ alkyl or aryl sulfonate (such as methane sulfonate or ethane sulfonate or benzenesulfonate) or a perfluoroalkylsulfonate (for example triflate).

The LG is preferably halogen or $C_1$-$C_{10}$ alkyl or aryl sulfonate, more preferably Br or $C_1$-$C_{10}$ alkyl sulfonate such as methane sulfonate or ethane sulfonate.

$R_1$ in compound (III) means OH or OProt, Prot means hydroxyl protecting group. $R_1$ is preferably OH group.

OProt group can be a suitable hydroxyl protective group, for example a hydroxyl protective group disclosed in Protective groups in organic synthesis, Theodora W. Greene and Petr G. M. Wuts, 3rd Ed., John Wiley & Sons Inc.

The reaction of compound (II) with compound (III), preferably compound (IIb) with compound (IIIa) can be performed in a suitable solvent in a presence of a base.

The solvent can be selected for example from N,N-dimethylformamide (DMF) or a poorly nucleophilic alcohol (secondary alcohol such as isopropanol or butan-2-ol) or dioxan or tetrahydrofurane (THF) or 2-methyl-tetrahydrofurane or acetonitrile or dimethylacetamide (DMAC) or an ether (such as dimethylether or diethylether) or a mixture thereof. The solvent is preferably N,N-dimethylformamide or a mixture of N,N-dimethylformamide with butan-2-ol.

The volume ratio between N,N-dimethylformamide and butan-2-ol can be between 8:1 and 15:1, preferably it is between 10:1 and 12:1.

The base can be selected from for example a carbonate (such as $Na_2CO_3$ or $K_2CO_3$ or $Rb_2CO_3$ or $Cs_2CO_3$) or a hydroxide (such as NaOH or KOH or CsOH or $Ba(OH)_2$ or TlOH (and their hydrates)) or an alkoxide (such as $NaOCH_3$ or NaOEt or TlOEt or NaOt-Bu or KOt-Bu) or a fluoride (such as NaF or KF or CsF or $Bu_4NF$) or an acetate (for example AcOK or AcONa) or other inorganic base (such as $K_3PO_4$) or an amine (such as $Et_3N$ or $(i-Pr)_2EtN$). The base is preferably potassium tert-butoxide (KOt-Bu) or sodium tert-pentoxide. The use of sodium tert-pentoxide as a base together with a solvent mixture comprising N,N-dimethylformamide and butan-2-ol improves the purity of obtained product by suppressing a formation of precipitates during addition of the base. The precipitates contribute to formation of impurities in the product. The use of given conditions also allows to perform the reaction at room temperature (20-25° C.).

The base is added to the solution of compound (III) or compound (IIIa) in the solvent. The concentration of compound of formula (III) in the solvent can be between 0.1 g/ml and 0.5 g/ml, preferably it is between 0.15 g/ml and 0.35 g/ml. In case when compound of formula (IIIb) is used, the concentration of compound of formula (IIIa) in the solvent or solvent mixture can be between 0.08 g/ml and 0.5 g/ml, preferably it is between 0.10 g/ml and 0.20 g/ml. The concentration of the base in the solvent can be between 0.04 g/ml and 0.5 g/ml, preferably it is between 0.06 g/ml and 0.25 g/ml, more preferably between 0.06 g/ml and 0.15 g/ml. The molar ratio between the base and the compound of formula (III) or the compound of formula (IIIa) can be between 1:1 and 2:1, preferably it is between 1:1 and 1:1.5. The solution of compound (III) or compound (IIIa) can be cooled before the base is added. It can be cooled to a temperature less than 10° C., preferably to a temperature between −10° C. and 5° C. But the base can be also added at a temperature between 20-25° C. The base can be added either in form of a solution in the reaction solvent or can be added in solid form in portions, such as in 5 or 6 or 7 or 8 or 9 or 10 and more portions. The mixture is stirred at the same temperature for between 10 and 120 minutes, preferably for between 10 and 30 minutes.

A solution of compound of formula (II) or the compound of formula (IIb) in a solvent is added at the same temperature. The solvent can be the same as used for compound of formula (III) or formula (IIIb) or it can be different.

The concentration of compound (II) in the solvent can be between 0.1 g/ml and 1 g/ml, preferably it is between 0.2 g/ml and 0.4 g/ml. In case the compound of formula (IIb) is used the concentration of compound (IIb) in the solvent can be between 0.05 g/ml and 1 g/ml, preferably it is between 0.05 g/ml and 0.2 g/ml. The molar ratio between compound (II) or compound (IIb) and compound (III) or compound (IIIa) can be between 1:1 and 1:2, preferably in is between 1:1 and 1:1.15. The solution of compound of formula (II) or compound of formula (IIb) is added for example in the course of 5 or 10 or 20 or 30 or 40 or 50 or 60 or 80 or 100 or 120 minutes. The mixture is then stirred at a temperature between −20° C. and 10° C., preferably at a temperature between 0° C. and 5° C. for between 10 and 180 minutes, preferably for between 10 and 60 minutes. The reaction progress can be monitored by a suitable analytical technique, e.g. by HPLC or GC. After the reaction is completed to the mixture water was added. The volume ratio between water and the solvent can be between 0.5:1 and 2:1, preferably it is between 1.2:1 and 2.5:1. The mixture can be washed several times, for example 2 or 3 or 4 or 5 or 6 times with a water non-miscible organic solvent, for example with toluene or an alkane such as heptane or pentane or hexane, preferably an alkane such as heptane or pentane or hexane, more preferably heptane is used. The volume ratio between the solvent used for washing and the volume of the washed mixture can be between 0.5:1 and 2:1, preferably it is between 0.15:1 and 0.5:1, more preferably it is between 0.2:1 and 0.3:1. The combined organic phases can be washed for example with water or brine or a mixture of water and N,N-dimethylformamide, preferably a mixture of water and N,N-dimethylformamide is used. The volume ratio between water and N,N-dimethylformamide can be between 1:0.3 and 1:1, preferably it is between 1:0.4 and 1:0.6. The washing step can be repeated for example 1×, 2×, 3×, 4× or more times. After the extraction the mixed organic phases can be dried for example using MgSO$_4$ and are concentrated to provide compound of formula (IV) in excellent purity and yield. Or alternatively the organic phases are mixed and mixed organic phase is mixed with a solvent that is suitable for oxidation reaction and is not miscible with the organic phase, for example acetonitrile or N,N-dimethylformamide or methanol. The volume ratio between the organic solvent and the solvent suitable for oxidation reaction 1:0.7 and 1:1.5, preferably it is between 1:0.8 and 1:1.2. Phases are separated and the phase containing the solvent suitable for oxidation is washed with an alkane such as heptane or pentane or hexane. The volume ratio between the alkane and the solvent suitable for oxidation can be between 0.3:1 and 1:1, preferably it is between 0.4:1 and 0.7:1. The washing can be repeated for example 1×, 2×, 3×, 4× or more times. The phases containing the alkane was mixed together and washed with the solvent suitable for oxidation. The volume ratio between the alkane and the solvent suitable for oxidation can be between 0.1:1 and 1:1, preferably it is between 0.2:1 and 1:1, preferably between 0.2:1 and 0.5:1. The phases containing the solvent suitable for oxidation are mixed together. Alternatively to described procedure the compound of formula (IV) can be dissolved in a solvent that is not miscible with an alkane such as acetonitrile or N,N-dimethylformamide or methanol and the solution is washed with an alkane as described above. Using the disclosed procedure not only provides the product compound of formula (IVa) in a solvent that is suitable for subsequent reaction step but also improves the purity of the product because the impurities are soluble in used alkane and are therefore removed from the product.

Compound of formula (II) can be prepared form a compound of formula (V),

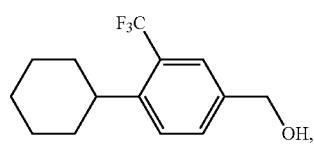

(V)

by reacting the compound of formula (V) in a suitable solvent either with a suitable halogenating agent or with a sulfonate compound (such as methansulfonic acid chloride or trifluoromethanesulfonic acid chloride or toluenesulfonic acid chloride or benzenesulfonic acid chloride). As a halogenating agent HCl or HBr or HI or PBr$_3$ or SOCl$_2$ or bromine or iodine or carbon tetrabromide or N-bromosuccinimide or N-iodosuccinimide can be used, preferably HBr in a presence of acetanhydride and acetic acid is used.

The halogenating reaction can be performed in a presence of a suitable activator like triphenylphosphine (PPh$_3$).

The reaction can be done in a suitable solvent, for example toluene or acetonitrile or water or acetic acid or nitromethane or halogenated alkanes (such as dichloromethane or chloroform) or an acetate (such as methylacetate or ethyl acetate or isopropyl acetate or iso-butyl acetate) or tetrahydrofurane or 2-methyl-tetrahydrofurane or 1,4-dioxane, preferably toluene is used.

The concentration of compound of formula (V) in the solvent can be between 0.05 g/ml and 0.5 g/ml, preferably it is between 0.1 and 0.3 g/ml. The molar ratio between the compound of formula (V) and the either sulfonate compound or the halogenating agent can be between 1:1 and 1:50, preferably it is between 1:1 and 1:10, more preferably it is between 1:1 and 1:5.

The compound of formula (V) is dissolved in the solvent and the either sulfonate compound or the halogenating agent is added to the mixture. The sulfonate compound or the halogenating agent are added either in portions or dropwise in the course of 5 or 10 or 20 or 30 or 40 or 50 or 60 or 90 or 120 minutes. The mixture is stirred at a temperature between 20° C. and the reflux temperature of the used solvent, preferably at a temperature between 20° C. and 50° C. for between 1 and 50 hours, preferably for between 10 and 30 hours. The reaction progress can be monitored by a suitable analytical technique, e.g. by HPLC or GC. After the reaction is completed the mixture is cooled to a temperature lower than 10° C., preferably to a temperature between −20° C. and 5° C., more preferably to a temperature between −5° C. and 5° C. To the mixture water is added in portions, preferably dropwise. The volume ratio between water and the used solvent can be between 1:0.5 and 1:5, preferably it is between 1:1 and 1:2. Then a water immiscible solvent, such as an alkane or an ether is added to the mixture, preferably an alkane such as heptane is used. The volume ratio between water and the water immiscible solvent can be between 1:1 and 1:10, preferably it is between 1:1 and 1:5, more preferably it is between 1:1 and 1:3. The mixture is warmed to a temperature between 20° C. and 25° C. and the phases are separated. The organic phase can be washed with water or with saturated aqueous solution of NaHCO$_3$. The organic phase is then mixed with silicagel and the mixture was stirred at the temperature between 20° C. and 25° C. for between 15 and 60 minutes, preferably for between 20 and 45 minutes. The concentration of the silicagel in the mixture can be between 0.003 g/ml and 0.02 g/ml, preferably it is between 0.005 g/ml and 0.15 g/ml.

Compound of formula (IIb) can be prepared from a compound of formula (V):

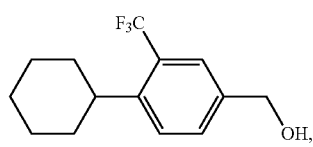

(V)

by reacting the compound of formula (V) in a suitable solvent (first organic solvent) in a presence of a base with an activated derivative of methane sulfonyl acid such as methane sulfonyl chloride or methane sulfonyl anhydride.

The reaction can be done in a suitable solvent, for example toluene or acetonitrile or nitromethane or halogenated alkane (such as dichloromethane or chloroform) or an acetate (such as methylacetate or ethyl acetate or isopropyl acetate or iso-butyl acetate) or 1,4-dioxane, preferably methyl tert-butyl ether is used.

As a base an amine base (such as triethyl amine or diisopropyl ethyl amine or 1,8-Diazabicyclo[5.4.0]undec-7-ene or 1,5-Diazabicyclo[4.3.0]non-5-ene) or a carbonate (such as $Na_2CO_3$ or $K_2CO_3$ or $Rb_2CO_3$ or $Cs_2CO_3$), preferably triethyl amine is used.

The molar ratio between the base and the compound of formula (V) can be between 1:1 and 5:1, preferably it is between 1:1 and 2:1.

The concentration of compound of formula (V) in the solvent can be between 0.1 g/ml and 1 g/ml, preferably it is between 0.2 and 0.6 g/ml. The molar ratio between the compound of formula (V) and the activated derivative of methane sulfonyl acid can be between 1:1 and 1:10, preferably it is between 1:1 and 1:5, more preferably between 1:1 and 1:2.

The compound of formula (V) is dissolved in the solvent together with the base. The mixture is cooled to a temperature between −30° C. and 10° C., preferably between −5° C. and 5° C. The activated derivative of methane sulfonyl acid is mixed with a solvent. The solvent can be the same as used for dissolution compound of formula (V) or can be selected for example from acetonitrile or an alcohol (such as ethanol) or halogenated solvent (such as dichloromethane). The temperature of the mixture is set to between 10° C. and 30° C., preferably between 25° C. and 30° C. and added to the previously prepared mixture of compound od formula (V) in the course between 30 and 180 minutes, preferably between 40 and 70 minutes. Obtained mixture is stirred at a temperature between −30° C. and 10° C., preferably at between −5° C. and 5° C. for between 30 minutes and 180 minutes, preferably between 30 minutes and 60 minutes. To the mixture an acid, for example HCl, was added to neutralized the remaining base. The molar ration between added acid and the base can be between 0.7:1 and 1.5:1, preferably it is between 0.1:1 and 1:1. After the acid addition the temperature of the mixture is set to between 20° C. and 30° C. and the mixture is stirred at this temperature for between 5 minutes and 60 minutes. The layers are separated. The addition of an acid can be repeated, for example 1×, 2×, 3× or more times. The organic phase is dried, for example using anhydrous $MgSO_4$. The organic phase can be optionally contacted with charcoal and filtered. The mixture is distilled at a temperature between 20° C. and 40° C. until more volatile solvent is removed. To the mixture a solvent selected from an alkane (such as heptane), preferably heptane is added. The volume ratio between the first organic solvent and the added alkane, preferably heptane, can be between 1:1.5 and 1:3, preferably it is between 1:1.6 and 1:2. The mixture was heated to a temperature between 70° C. and 90° C. to obtain a clear solution. The mixture was cooled to a temperature between 50° C. and 65° C. and stirred at this temperature form between 30 and 180 minutes to start the crystallization of the product. The mixture was cooled to a temperature between −30° C. and 10° C., preferably to a temperature between 0° C. and 5° C. and stirred at this temperature for between 30 and 180 minutes. The mixture was filtered off to provide a solid crystalline compound (IIb).

We have surprisingly found that compound of formula (IIb) can be isolated in crystalline form. That offers further possibility for purification compound of formula (IIb) and final compound of formula (I). The crystalline form can be characterized by XRPD pattern having 2θ values 4.7°, 14.5° and 21.3° degrees 2 theta (±0.2 degrees 2 theta). The solid form can be further characterized by XRPD pattern described in following table:

| Angle 2-Theta ° | Intensity % |
|---|---|
| 4.7 | 28.5 |
| 13.9 | 6.9 |
| 14.1 | 9.7 |
| 14.3 | 2.4 |
| 14.5 | 35.0 |
| 15.4 | 2.5 |
| 16.6 | 8.9 |
| 17.1 | 2.6 |
| 17.3 | 1.1 |
| 17.6 | 1.4 |
| 18.1 | 23.6 |
| 18.4 | 12.9 |
| 18.8 | 4.3 |
| 19.4 | 13.2 |
| 19.7 | 2.0 |
| 20.0 | 1.5 |
| 20.3 | 23.9 |
| 20.7 | 15.0 |
| 21.3 | 100.0 |
| 21.5 | 11.7 |
| 21.7 | 11.7 |
| 22.1 | 26.9 |
| 23.2 | 2.5 |
| 23.3 | 14.0 |
| 23.7 | 5.5 |
| 24.2 | 0.9 |
| 25.1 | 3.1 |
| 26.0 | 3.8 |
| 26.1 | 3.0 |
| 27.3 | 2.1 |
| 28.0 | 5.7 |
| 28.7 | 3.3 |
| 29.2 | 2.5 |
| 30.0 | 0.7 |
| 30.1 | 0.7 |
| 30.4 | 1.6 |
| 31.1 | 2.1 |
| 31.2 | 2.4 |
| 31.6 | 1.6 |
| 32.2 | 0.9 |
| 32.9 | 0.7 |
| 33.0 | 0.9 |
| 33.1 | 1.2 |
| 33.2 | 1.3 |
| 33.7 | 1.0 |
| 33.8 | 1.4 |
| 33.9 | 2.3 |
| 34.0 | 2.5 |
| 34.3 | 2.5 |
| 34.5 | 2.9 |
| 34.5 | 4.1 |

Figure 3:
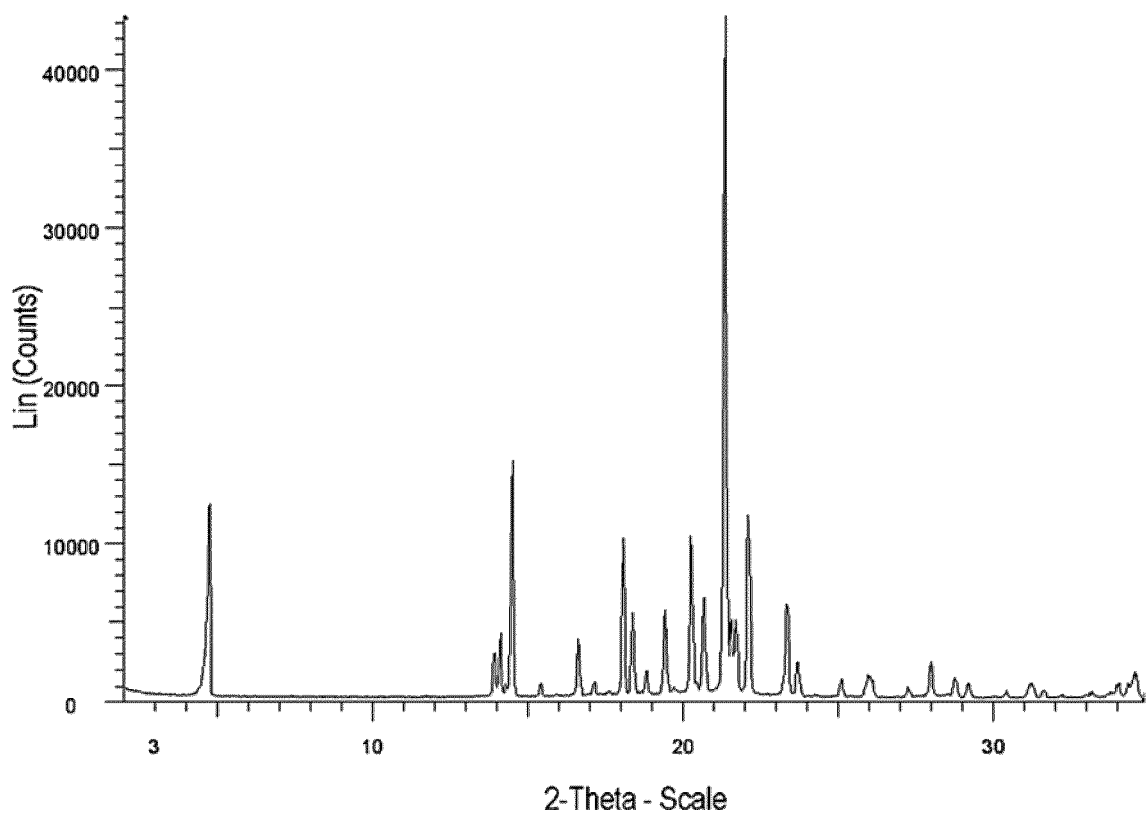
FIG. 3: XRPD pattern of the solid form of compound of formula (IIb) prepared according to Example 7.

The crystalline form can be further characterized by XRPD pattern depicted in FIG. 3.

In the process described in WO2013/113915 compound (IIa) is used:

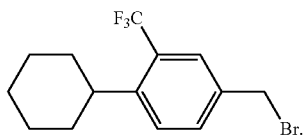
(IIa)

Compound of formula (IIa) prepared according to a process described in WO2013/113915 is an oil. We have surprisingly found that the compound of formula (IIa) can be isolated as a solid compound by a process comprising:
a. Dissolving the compound of formula (IIa) in a solvent;
b. Concentrating the solution obtained in step a. at a temperature less than 25° C. to obtain solid compound of formula (IIa).

The solvent in step a. can be any suitable solvent able to dissolved the compound of formula (IIa) for example toluene or $C_{5-10}$ alkanes (such as heptane or hexane or pentane) or acetonitrile or acetic acid or nitromethane or a halogenated alkanes (such as dichloromethane, chloroform) or an acetate (such as methylacetate or ethyl acetate or isopropyl acetate or iso-butyl acetate) or tetrahydrofurane or 2-methyl-tetrahydrofurane or an alcohol (such as methanol or ethanol or butanol or 2-butanol or tert-butanol or isopropanol or tert-amyl alcohol or amyl alcohol) or 1,4-dioxane, preferably toluene or an $C_{5-10}$ alkane (such as heptane or hexane or pentane) is used.

The temperature in step b. can lower than 25° C. or 15° C. or 10° C. or 5° C. or 0° C. or −10° C. or −20° C. or −30° C.

The concentrating step b. can be done either at a temperature lower than 25° C. during the whole concentrating procedure or the concentrating procedure can be started an elevated temperature for example between 30° C. and 60° C. and the mixture can be than cooled to a temperature less than 25° C. at the end of the concentrating procedure. The concentrating procedure is done for example by using vacuum, for example between 30 and 100 mbar. The concentrating step is done until the solid form of compound of formula (IIa) is obtained.

The solid form of compound of formula (IIa) can be characterized by XRPD pattern having 2θ values 16.9°, 18.9°, 19.9°, 23.3° degrees 2 theta (±0.2 degrees 2 theta). The solid form of compound of formula (IIa) can be further characterized by XRPD pattern having 2θ values 8.6°, 14.0°, 14.9°, 16.9°, 18.9°, 19.9°, 23.3° degrees 2 theta (±0.2 degrees 2 theta). The solid form of compound of formula (IIa) can be also characterized by XRPD pattern having 2θ values (±0.2 degrees 2 theta) stated in following table.

| Angle 2-Theta ° | Intensity % |
|---|---|
| 8.6 | 21.7 |
| 10.8 | 12.6 |
| 11.5 | 14.3 |
| 13.7 | 11.0 |
| 14.0 | 15.7 |
| 14.9 | 29.6 |
| 15.6 | 12.1 |
| 16.9 | 30.5 |
| 17.4 | 27.7 |
| 18.1 | 22.7 |
| 18.9 | 55.0 |
| 19.2 | 41.7 |
| 19.7 | 13.0 |
| 19.9 | 87.4 |
| 20.8 | 10.7 |
| 21.5 | 13.4 |
| 22.0 | 19.3 |
| 22.3 | 25.0 |
| 22.9 | 47.0 |
| 23.3 | 100.0 |
| 23.8 | 24.6 |
| 24.5 | 11.6 |
| 24.9 | 8.1 |
| 26.2 | 9.9 |
| 26.7 | 8.7 |
| 27.2 | 8.8 |
| 27.6 | 14.2 |
| 27.9 | 10.9 |
| 28.4 | 9.6 |
| 29.2 | 8.3 |
| 29.6 | 11.3 |
| 30.4 | 17.3 |
| 31.2 | 11.1 |
| 31.6 | 15.2 |
| 32.4 | 10.9 |
| 34.0 | 9.8 |
| 34.3 | 10.1 |

Figure 2:
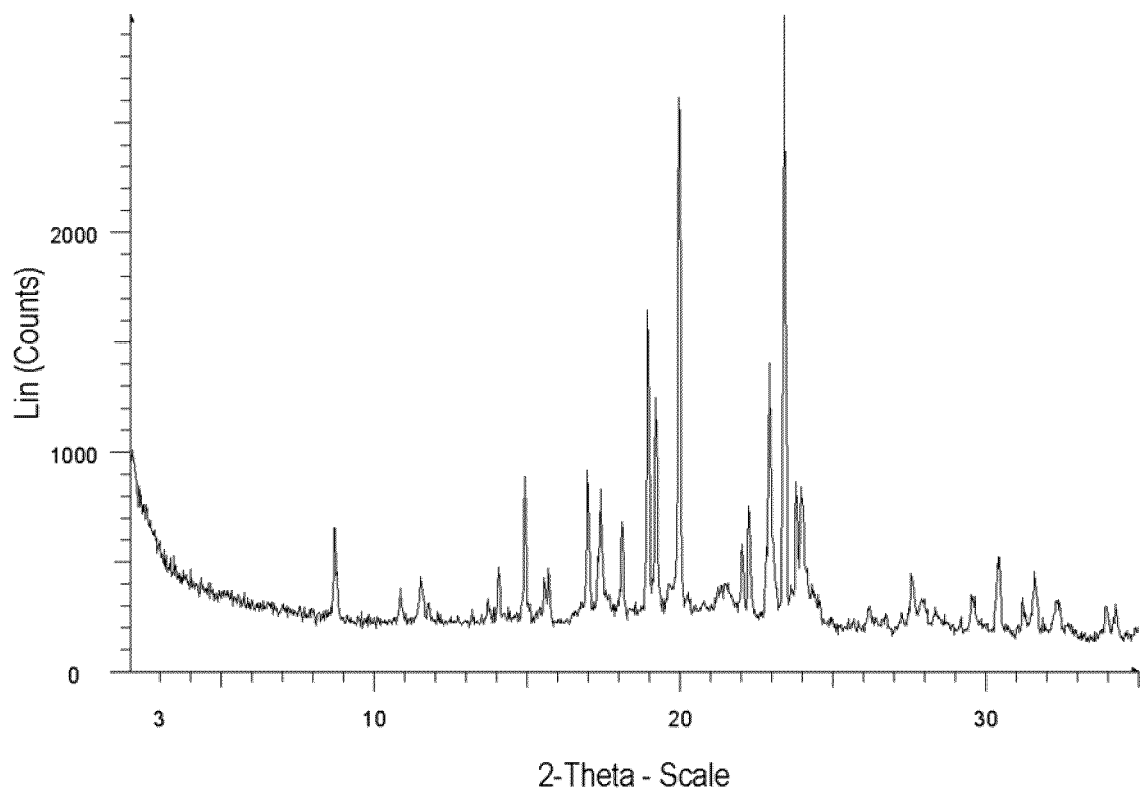
FIG. 2: XRPD pattern of the solid form of compound of formula (IIa) prepared according to Example 1.

The isolated solid form of compound of formula (IIa) can be also characterized by XRPD pattern depicted in FIG. 2.

The compound of formula (III) can be prepared by a process comprising:
a. Reacting compound of formula (VI) with hydroxylamine or a salt (for example HCl salt) thereof in a solvent. In case hydroxylamine is used in a form of a salt also a suitable base is used in the reaction mixture:

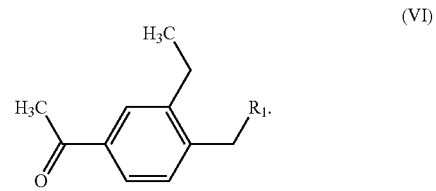
(VI)

$R_1$ means OH or OProt, Prot means hydroxyl protective group.

The compound of formula (VI) is preferably compound of formula (VIa),

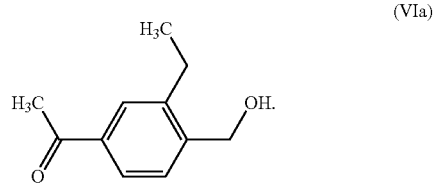
(VIa)

The solvent used in step a. can be for example an alcohol (such as methanol or ethanol or propanol or iso-propanol or butanol or tert-butanol or pentanol or hexanol) or water or a halogenated solvent (such as dichloromethane or tetrachloromethane or tetrachloroethane) or tetrahydrofurane or 2-methyl-tetrahydrofurane or N,N-dimethylformamide (DMF) or dimethylacetamide or pyridine or 1,4-dioxane or an acetate (such as ethyl acetate or methylacetate or propylacetane) or toluene. Preferably an alcohol, more preferably methanol is used. As a suitable base a carbonate (such as $Na_2CO_3$ or $K_2CO_3$ or $Rb_2CO_3$ or $Cs_2CO_3$) or an acetate (for example AcOK or AcONa) or a phosphate (such as $K_3PO_4$) or an amine (such as $Et_3N$, $(i-Pr)_2EtN$) can be used. Preferably sodium acetate is used.

The concentration of compound of formula (VI) or compound of formula (VIa) in the solvent can be between 0.05 g/ml and 1 g/ml, preferably it is between 0.1 g/ml and 0.5 g/ml, more preferably between 0.1 g/ml and 0.3 g/ml. The concentration of the base in the solvent can be between 0.01 g/ml and 0.5 g/ml, preferably it is between 0.01 and 0.1 g/ml, more preferably between 0.03 and 0.08 g/ml. The molar ratio between the base and the hydroxylamine or hydroxylamine salt can be between 1:1 and 5:1, preferably it is between 1:1 and 2:1, more preferably it is between 1.1:1 and 1.5:1. The molar ratio between hydroxylamine or a salt thereof and the compound of formula (VI) or the compound of formula (VIa) can be between 1.05:1 and 2:1, preferably it is between 1.1:1 and 1.5:1.

Compound of formula (VI) or compound of formula (VIa) is dissolved in the solvent. To the mixture, the base and the hydroxylamine or a salt thereof are added. The resulting mixture is stirred at a temperature between 10° C. and 50° C., preferably at a temperature between 20° C. and 30° C. for between 40 and 300 minutes, preferably for between 60 and 120 minutes. The reaction progress can be monitored by a suitable analytical technique, e.g. by HPLC or GC.

We have surprisingly found that compound of formula (III) preferably compound of formula (III) wherein R1 means OH, i.e. compound of formula (IIIa) can be isolated in a solid form. That offers further purification of compound of formula (IIIa) or formula (III) and final compound of formula (I),

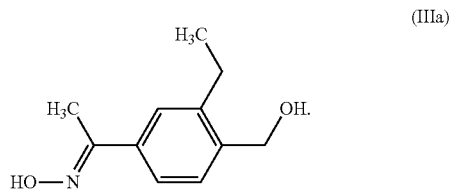

(IIIa)

The compound of formula (IIIa) or (III) can be isolated from the reaction mixture after the reaction is finished by a process comprising addition of water into the reaction mixture. The volume ratio between the added water and the solvent used in the reaction can be between 1:1 and 3:1, preferably it is between 1:1 and 2:1. The mixture is stirred at a temperature between 20° C. and 30° C. for between 10 and 240 minutes, preferably for between 10 and 60 minutes. Other water can be further added to the mixture. The volume ratio between the further added water in this step and the solvent used in the reaction can be between 0.1:1 and 1:1, preferably it is between 0.2:1 and 0.5:1. The mixture is cooled to a temperature between −20° C. and 10° C., preferably to a temperature between −5° C. and 5° C. and stirred at this temperature for between 1 and 5 hours, preferably for between 1 and 2 hours. The precipitated solid form of compound of formula (IIIa) or (III) is isolated by any suitable technique, for example by filtration in excellent yield and quality.

Alternatively, the solid form of compound of formula (III) preferably compound of formula (IIIa) can be prepared by following process. After the reaction is completed the reaction mixture is concentrated to approx. ¼ and ½ of the original volume, preferably to approx. ¼ of the original volume. The rest is dissolved in a mixture of saturated water solution of a base, for example $NaHCO_3$ and water non-miscible solvent, for example ethylacetate or methylacetate or toluene or an ether. The volume ration between the base solution and the water non-miscible solvent can be between 1:1 and 1:3, preferably it is between 1:1 and 1:2. The phases are separated and the water phase is extracted several times with the water non-miscible solvent. The combined organic phases can be washed with water, dried over $MgSO_4$ and concentrated to provide compound of formula (III) or formula (IIIa) in excellent yield and quality.

In case $R_1$ means OProt, the compound of formula (III) can be deprotected by using either an acid (such as HCl or HBr or trifluoroacetic acid or toluenesulfonic acid) or a base (such as a hydroxide (for example NaOH or KOH or LiOH) or a carbonate (for example $K_2CO_3$ or $Na_2CO_3$)) or using an oxidative agent (such as 2,3-Dichloro-5,6-dicyano-1,4-benzoquinone (DDQ)) or using hydrogenation deprotection (for example with $H_2$ in a presence of a catalyst such as Pt or Pd or Ni) to provide compound of formula (III) where $R_1$ means OH. The compound of formula (III) where $R_1$ means OProt can also be used in the subsequent reaction step with compound of formula (II) to provide compound of formula (IV) wherein $R_1$ means OProt.

The solid form of compound of formula (IIIa) prepared according to presented processes can be characterized by XRPD pattern having 2θ values 12.2°, 19.1°, 20.9°, 24.6° degrees 2 theta (±0.2 degrees 2 theta). The solid form of compound of formula (IIIa) can be further characterized by XRPD pattern having 2θ values 10.9°, 12.2°, 14.9°, 19.1°, 20.9°, 24.6° degrees 2 theta (±0.2 degrees 2 theta). The isolated solid form of compound of formula (IIIa) can be also characterized by XRPD pattern having 2θ values (±0.2 degrees 2 theta) stated in following table.

| Angle 2-Theta ° | Intensity % |
|---|---|
| 10.9 | 4.9 |
| 11.8 | 2.5 |
| 12.2 | 100.0 |
| 14.9 | 6.9 |
| 15.4 | 1.4 |
| 18.2 | 1.2 |
| 18.6 | 2.1 |
| 19.1 | 11.9 |
| 19.4 | 1.9 |
| 19.9 | 5.3 |
| 20.3 | 2.4 |
| 20.9 | 9.7 |
| 21.3 | 1.2 |
| 21.7 | 2.5 |
| 22.1 | 3.1 |
| 22.9 | 2.3 |
| 23.2 | 2.1 |
| 23.8 | 3.2 |
| 24.6 | 31.4 |
| 25.0 | 19.6 |
| 25.3 | 17.8 |
| 26.4 | 1.5 |
| 26.9 | 4.2 |
| 27.5 | 4.8 |
| 29.1 | 2.6 |
| 29.4 | 1.9 |
| 29.8 | 0.9 |
| 30.2 | 0.9 |
| 30.4 | 1.7 |
| 31.1 | 0.8 |

| Angle 2-Theta ° | Intensity % |
| --- | --- |
| 31.4 | 2.4 |
| 31.8 | 0.6 |
| 32.7 | 0.7 |
| 32.9 | 1.7 |
| 33.3 | 0.9 |
| 33.6 | 2.1 |
| 34.7 | 0.6 |

The isolated solid form of compound of formula (IIIa) can be also characterized by XRPD pattern depicted in FIG. 1.

Compound of formula (IV) can be transformed into siponimod or a salt thereof for example by a process comprising:

a. In case $R_1$ in compound of formula (IV) means OProt, deprotecting the Prot group to obtain compound of formula (IV) wherein $R_1$ means OH, compound of formula (IVa);

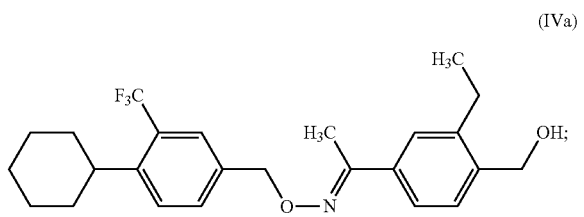

(IVa)

b. Reacting compound of formula (IV) wherein $R_1$ means OH, i.e. compound of formula (IVa) with an oxidation agent to obtain compound of formula (VII),

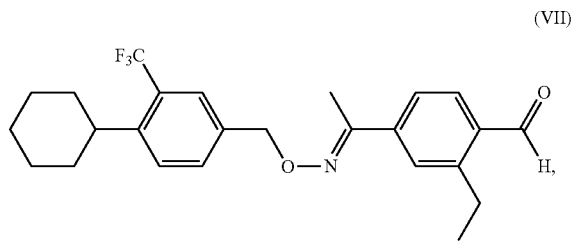

(VII)

c. Reacting compound of formula (VII) with compound of formula (VIII) in a presence of a reducing agent in a solvent to obtain compound of formula (I),

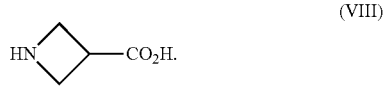

(VIII)

In the step a. the deprotecting can be done by a suitable acid (such as HCl or HBr or trifluoroacetic acid or toluenesulfonic acid) or a base (such as a hydroxide (for example NaOH or KOH or LiOH) or a carbonate (for example $K_2CO_3$ or $Na_2CO_3$)) or using an oxidative agent (such as 2,3-Dichloro-5,6-dicyano-1,4-benzoquinone (DDQ)) or using hydrogenation (for example with $H_2$ in a presence of a catalyst such as Pt or Pd or Ni).

The reaction step b. can be performed in a suitable solvent (such as toluene or an acetate (such as ethylacetate or methylacetate) or acetonitirile or an alkane (such as hexane or heptane or cycloheptane or cyclohexane) or N,N-methyl pyrollidone or N,N-dimethylformamide or a chlorinated solvent (such as dichloromethane or chloroform) or a mixture thereof by an oxidating agent (such as oxygen or 2,2,6,6-tetramethylpiperidine 1-oxyl, TEMPO, or poly[6-(1,1,3,3-tetramethylbutyl)amino]-1,3,5-triazine-2,4-diyl][2,2,6,6-tetramethyl-1-oxy-4-piperidinyl)iminol-1,6-hexanediyl [(2,2,6,6-tetramethyl-1-oxy-4-piperidinyl)imino]]), PIPO, in a presence of KBr and KHCO3 and sodium hypochlorite, or MnO2), preferably oxygen is used. The reaction step b. can be done in a presence of a catalyst such as CuI in a presence of 2,2'-bypiridine. In preferred embodiments following combination of agents, catalysts and solvents can be used:

1. TEMPO in a presence of NaOCl and KBr and a hydrogen carbonate (for example sodium or potassium) in a solvent selected for example from toluene or an alkane (such as heptane) or an acetate (such as ethyl acetate or isopropyl acetate) or a combination thereof in a presence of water;
2. $MnO_2$ in a solvent selected for example from an alkane (such as heptane or hexane) or a halogenated solvent (such as dichloromethane or chloroform) or a combination thereof
3. TEMPO in a presence of oxygen and CuI and 2,2'-bypiridine and N-methylimidazole and a solvent selected for example from acetonitrile or N,N-methyl pyrollidone or N,N-dimethylformamide or a combination thereof.

The molar ration between the catalyst and compound of formula (IVa) can be between 0.04:1 and 0.15:1, preferably it is between 0.05:1 and 0.07:1. The concentration of compound of formula (IVa) in the solvent can be between 0.04 g/ml and 0.2 g/ml, preferably it is between 0.06 g/ml and 0.15 g/ml.

The reaction is performed at a temperature between −20° C. and 100° C., for between 30 and 300 minutes. The reaction progress can be monitored by a suitable analytical technique, e.g. by HPLC or GC.

To the mixture water is added to obtain a suspension. The weight ratio between added water and the solvent used in step b. can be between 1:1 and 2:1. The mixture is then stirred for between 30 minutes and 120 minutes and filtered off and the obtained solid can be optionally dried. The obtained solid crystalline compound (VII) can be characterized by XRPD pattern having 2θ values 9.6°, 16.3° and 19.6° degrees 2 theta (±0.2 degrees 2 theta). The solid form of compound of formula (VII) can be further characterized by XRPD pattern having 2θ values 9.6°, 16.3°, 18.3°, 19.0° and 19.6° degrees 2 theta (±0.2 degrees 2 theta). The isolated solid form of compound of formula (VII) can be also characterized by XRPD pattern having 2θ values (±0.2 degrees 2 theta) stated in following table.

| Angle 2-Theta ° | Intensity % |
| --- | --- |
| 7.7 | 12.2 |
| 9.2 | 11.6 |
| 9.6 | 100.0 |
| 10.0 | 7.7 |
| 10.7 | 7.4 |
| 11.8 | 3.2 |
| 12.9 | 13.6 |
| 13.2 | 16.2 |
| 15.7 | 5.8 |

| Angle 2-Theta ° | Intensity % |
|---|---|
| 15.9 | 13.9 |
| 16.3 | 99.5 |
| 16.7 | 3.9 |
| 17.1 | 13.6 |
| 17.7 | 2.9 |
| 18.3 | 26.7 |
| 18.8 | 6.0 |
| 19.0 | 23.9 |
| 19.3 | 8.9 |
| 19.6 | 47.3 |
| 20.2 | 41.2 |
| 20.8 | 10.9 |
| 21.5 | 6.5 |
| 22.3 | 16.3 |
| 23.3 | 12.8 |
| 23.8 | 4.4 |
| 24.5 | 7.9 |
| 24.8 | 65.6 |
| 25.0 | 48.2 |
| 25.6 | 3.0 |
| 25.9 | 5.2 |
| 26.3 | 7.2 |
| 26.7 | 15.5 |
| 27.3 | 3.1 |
| 27.7 | 3.9 |
| 28.3 | 4.7 |
| 29.0 | 2.3 |
| 29.4 | 2.2 |
| 30.4 | 3.5 |
| 31.2 | 4.0 |
| 31.4 | 3.3 |
| 32.0 | 3.8 |
| 32.5 | 3.3 |
| 32.8 | 2.6 |
| 33.2 | 3.4 |
| 33.7 | 1.9 |
| 34.0 | 2.4 |
| 34.6 | 2.9 |

Figure 4:
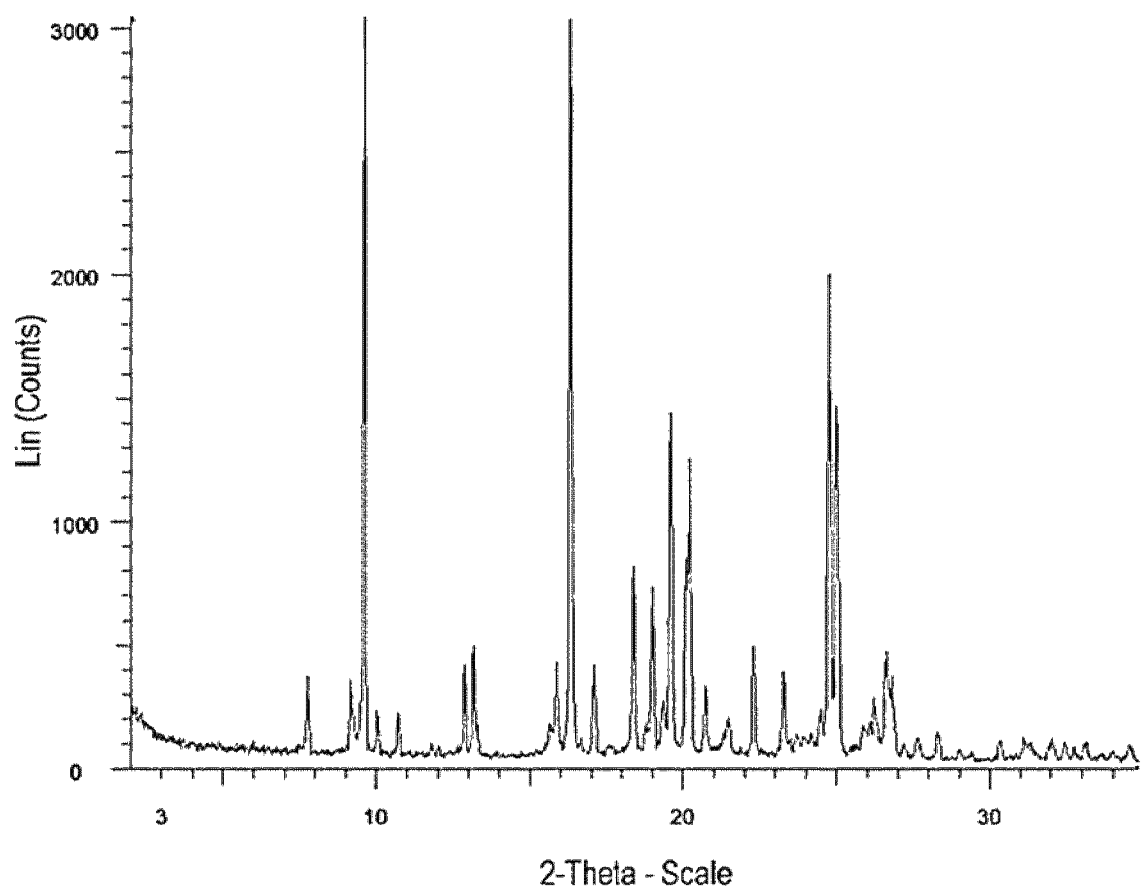
FIG. 4: XRPD pattern of the solid form of compound of formula (VII) prepared according to Example 9 or 10.

The crystalline form can be further characterized by XRPD pattern depicted in FIG. 4. The purity of the he solid compound of formula (VII) can be improved by crystallization form a mixture of acetonitrile in a mixture with water. The volume ration between acetonitrile and water can be between 5:1 and 10:1, preferably it is between 6:1 and 8:1. The concentration of compound of formula (VII) in the acetonitrile can be between 0.04 g/ml and 0.2 g/ml, preferably it is between 0.06 g/ml and 0.1 g/ml. The compound of formula (VII) is mixed with acetonitrile and water and the mixture is cooled to a temperature between 0° C. and 20° C., preferably between 10° C. and 15° C. and stirred at this temperature for between 30 minutes and 90 minutes. Solid crystalline compound of formula (VII) is filtered off and optionally dried.

The solvent in the reaction step c. can be selected from an alcohol (such as methanol or ethanol or propanol or isopropanol or butanol or tert-butanol). The reducing agent can be selected for example from a triacetoxyborohydride (such as sodium triacetoxyborohydride) or a cyanoborohydride (such as sodium cyanoborohydride) or $H_2$ in a presence of a catalyst (such as Pt or Pd or Ni) or triethylamine-$BH_3$ ($Et_3N$—$BH_3$) complex. Preferably triethylamine-$BH_3$ ($Et_3N$—$BH_3$) complex is used. When triethylamine-$BH_3$ complex is used for reduction the purity of product is higher comparing to reducing agent described in prior art. The reducing agent is preferably added in several portions, for example in 4 or 5 or 6 or 7 or 8 or 9 or 10 or more portions.

The compound of formula (VII) is mixed with the solvent and compound of formula (VIII) is added. The concentration of compound (VII) in the solvent can be between 0.02 g/ml and 0.2 g/ml, preferably it is between 0.03 and 0.1 g/ml. The molar ratio between the compound of formula (VII) and the compound of formula (VIII) can be between 1:1.1 and 1:3, preferably it is between 1:1.1 and 1:2. The mixture was stirred for between 15 and 120 minutes, preferably for between 20 and 60 minutes at a temperature between 20° C. and 30° C. The reducing agent was then added in portions in between 5 and 60 minutes. The mixture can be further stirred at this temperature for between 5 and 60 minutes. The reaction progress can be monitored by a suitable analytical technique, e.g. by HPLC or GC. After the reaction is finished the mixture is concentrated. The rest is dissolved in a mixture of water and water non-miscible solvent (for example ethylacetate or methylacetate or toluene or an ether). pH of the mixture is set to approx. 6 using for example aqueous solution of NaOH. The phases are separated, the organic phase is washed with water, dried using for example $MgSO_4$. The rest is dissolved in ethanol, the solution was concentrated to approx. between ¼ and ½, preferably to ½ of the original volume and dried for example using $MgSO_4$ and concentrated. The procedure can be repeated for example 2 or 3 or 4 or 5 or 6 times. To the rest an alkane, for example heptane or hexane or pentane, was added and the solution was concentrated to dryness to provide the compound of formula (I), Siponimod, in excellent yield and purity.

The overall yield of the presented process calculated on compound 4-(bromomethyl)-1-cyclohexyl-2-(trifluoromethyl)benzene is between 69 and 71% of the theoretical yield. That is significantly higher than the overall yield (26% of the theoretical yield) of the prior art process disclosed in WO2013/113915. The presented process also provides a process for isolation of two intermediates in solid form that provides a possibility for further purification.

The invention will be further illustrated by the following, non-limiting, examples.

EXAMPLES

Nuclear magnetic resonance spectroscopy (NMR) was performed using Avance III 400 MHz NMR spectrometer.

XRPD spectrum of solid compounds was obtained using the following measurement conditions:

Panalytical Empyrean diffractometer with Θ/2Θ geometry (transmission mode), equipped with a PixCell 3D detector

| | |
|---|---|
| Start angle (2Θ): | 2.0° |
| End angle (2Θ): | 35.0° |
| Step size: | 0.026° |
| Scan speed: | 0.0955°/seconds |
| Radiation type: | Cu |
| Radiation wavelengths: | 1.5406Å (Kα1), primary monochromator used |
| Divergence slit: | ½° |
| Antiscatter slit: | ½° |
| Soller slit: | 0.02 rad |
| Detector slit: | 7.5 mm |
| Rotation speed: | 30 rpm |

Example 1: Preparation of 4-(bromomethyl)-1-cyclohexyl-2-(trifluoromethyl)benzene

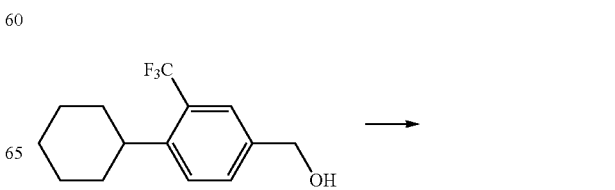

-continued

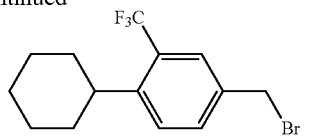

3.2 g of (4-cyclohexyl-3-(trifluoromethyl)phenyl)methanol was mixed with 22 ml of toluene. To the solution 12.8 ml of Hydrobromic acid (33% sol. in AcOH) was added at 20° C.-25° C. dropwise in course of 10 minutes with stirring. Then, 1.3 ml of Acetic anhydride was added with stirring at 20° C.-25° C. The resulting mixture was stirred at 20° C.-25° C. for 21 hours. The mixture was cooled to 0-2° C. and 30 ml of water was slowly added while the temperature of the mixture was kept below 20° C. 60 ml of n-heptane was added and the mixture was allowed to warm to 20° C.-25° C. The phases were separated and the organic phase was washed consecutively with 30 ml of water, 30 ml of saturated aqueous $NaHCO_3$ and 30 ml of water. The organic phase was mixed with 0.6 g of silica gel. The suspension was agitated for 20 minutes. The suspension was filtered and the filtrate was concentrated (40-50° C., 80→40 mbar, then 5-10° C., 20 mbar). 3.69 g of 4-(bromomethyl)-1-cyclohexyl-2-(trifluoromethyl)benzene was obtained as white solid in 92% yield and 99.3% purity (HPLC in, 235 nm). XRPD of the obtained solid compound corresponds to XRPD pattern depicted in FIG. 2.

Example 2: (E)-1-(3-ethyl-4-(hydroxymethyl)phenyl)ethan-1-one oxime

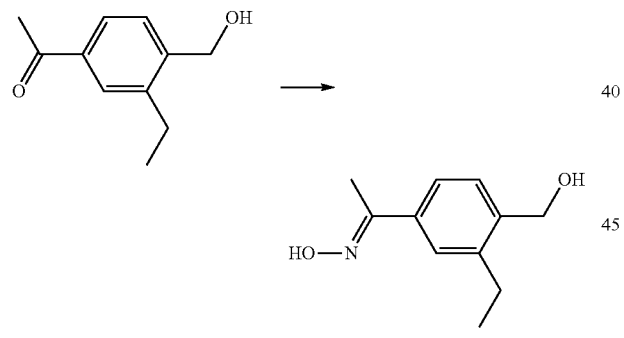

15 g of 1-(3-ethyl-4-(hydroxymethyl)phenyl)ethan-1-one was dissolved in 150 ml of methanol. The solution was cooled to 0-5° C. and 8.3 g sodium acetate followed by 7 g of hydroxylamine hydrochloride were added. The mixture was stirred at 0-5° C. for 5 minutes, the mixture was warmed to 20° C.-25° C. over approx. 70 minutes. The mixture was stirred for 110 minutes in total. The mixture was diluted with 150 ml of water at 20-25° C. and stirred for 20 minutes. Another 50 ml of water was added and the mixture was cooled to 0-2° C. It was stirred at this temperature for 1 hour. The formed solid was collected by filtration, washed with 25 ml of cold water and dried to provide 13.4 g (82% of the theoretical yield) of (E)-1-(3-ethyl-4-(hydroxymethyl)phenyl)ethan-1-one oxime as white solid, in 99.75% purity (HPLC in). XRPD of the obtained solid compound corresponds to XRPD pattern depicted in FIG. 1.

Example 3: (E)-1-(3-ethyl-4-(hydroxymethyl)phenyl)ethan-1-one oxime

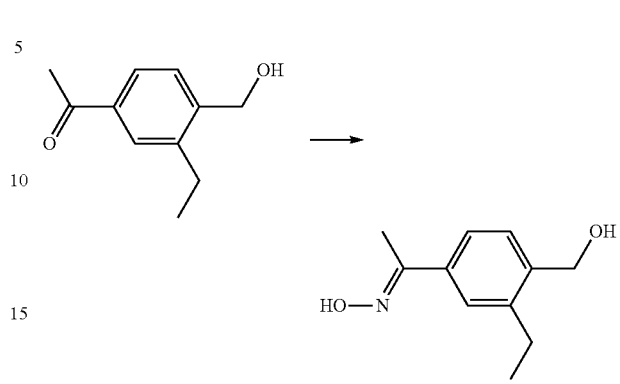

15 g of 1-(3-ethyl-4-(hydroxymethyl)phenyl)ethan-1-one was dissolved in 150 ml of methanol and 8.3 g sodium acetate followed by 7 g of hydroxylamine hydrochloride were added. The resulting mixture was stirred at 20° C.-25° C. for 60 minutes. The mixture was concentrated to the amount approx. 60 g. 150 ml of saturated aqueous $NaHCO_3$ and 90 ml of ethyl acetate were added, the phases were separated and the aqueous phase was extracted twice with 90 ml of ethyl acetate. The combined organic phases were washed with 90 ml of water. The organic phase was dried using $MgSO_4$, filtered and the filtrate was concentrated to approx. ½ of the original volume. It was diluted with 180 ml of toluene. The mixture was concentrated to the amount approximately 90 g. The suspension was stirred overnight at 20° C.-25° C. The mixture was filtrated and the obtained solid was dried to provide 14.11 g (86% of the theoretical yield) of (E)-1-(3-ethyl-4-(hydroxymethyl)phenypethan-1-one oxime with 99.7% purity (HPLC in). XRPD of the obtained solid compound corresponds to XRPD pattern depicted in FIG. 1.

Example 4: (E)-1-(3-ethyl-4-(hydroxymethyl)phenyl)ethan-1-one O-(4-cyclohexyl-3-(trifluoromethyl)benzyl) oxime

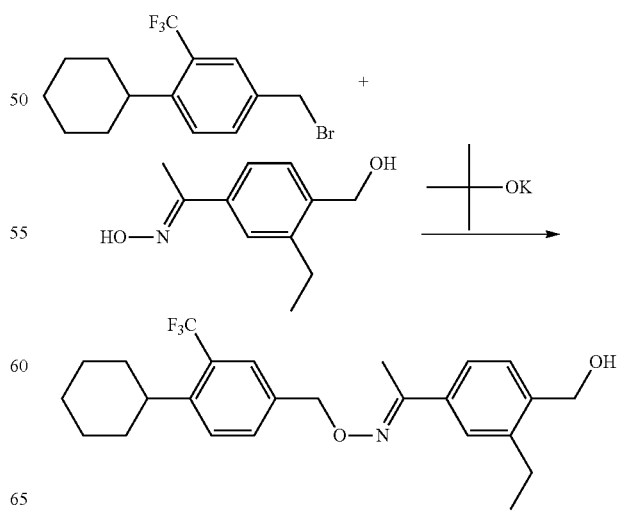

13.4 g of 1-(3-ethyl-4-(hydroxymethyl)phenyl)ethan-1-one oxime was dissolved in 70 ml of DMF at 20° C.-25° C. The solution was cooled down to 0-2° C. and 8.62 g of potassium tert-butoxide was added in approximately 8 equal portions. The suspension was stirred for 10 min and then, solution of 24.2 g of 4-(bromomethyl)-1-cyclohexyl-2-(trifluoromethyl) benzene in 70 ml of DMF was added over approximately 10 minutes while the temperature was kept below 10° C. The resulting mixture was stirred at 0-5° C. for 15 minutes. The mixture was diluted with 250 ml of water and it was extracted four times with 100 ml of toluene. The combined organic phase was washed twice with 200 ml of water and then with 200 ml of saturated aqueous NaCl. Washed organic phase was dried using MgSO₄, filtered and concentrated. The rest was diluted in 100 ml of n-heptane/EtOAc (10:1) and was passed through a short pad of silica gel (1 cm, preconditioned with n-heptane/EtOAc 10:1). The silica gel was washed with 300 ml of n-heptane/EtOAc 10:1. The combined filtrates were concentrated and dried to provide 29 g (88% of the theoretical yield) of (E)-1-(3-ethyl-4-(hydroxymethyl)phenyl)ethan-1-one O-(4-cyclohexyl-3-(trifluoromethyl)benzyl) oxime in form of yellowish oil, 99.3% purity (HPLC in).

Example 5: (E)-4-(1-(((4-cyclohexyl-3-(trifluoromethyl)benzyl)oxy)imino)ethyl)-2-ethylbenzaldehyde

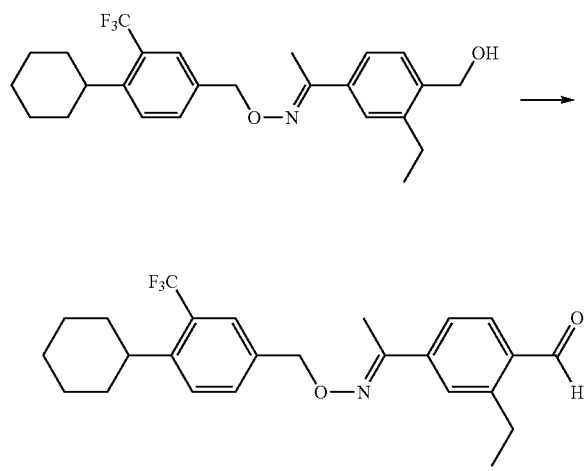

28.6 g of (E)-1-(3-ethyl-4-(hydroxymethyl)phenyl)ethan-1-one O-(4-cyclohexyl-3-(trifluoromethyl)benzyl) oxime was dissolved in 250 ml of n-heptane at 20° C.-25° C. 40.5 g of activated manganese(IV) oxide was added in 5 equal portions at 20° C.-25° C. The resulting suspension was heated to 80° C. and it was vigorously stirred at this temperature for 60 minutes. Then, the mixture was cooled to 20° C.-25° C., diluted with 250 ml of n-heptane and the suspension was filtered through a 0.5 cm pad of silica gel (pre-conditioned with n-heptane). The residual solids in the flask were suspended in 200 ml of n-heptane. The silica gel was washed with this suspension. The silica gel was washed with 200 ml of ethyl acetate. The combined filtrates were concentrated to dryness to provide 26.1 g (91% of theoretical yield) of (E)-4-(1-(((4-cyclohexyl-3-(trifluoromethyl)benzypoxy)imino)ethyl)-2-ethylbenzaldehyde as yellow solid, 99.0% purity (HPLC in).

Example 6: Siponimod

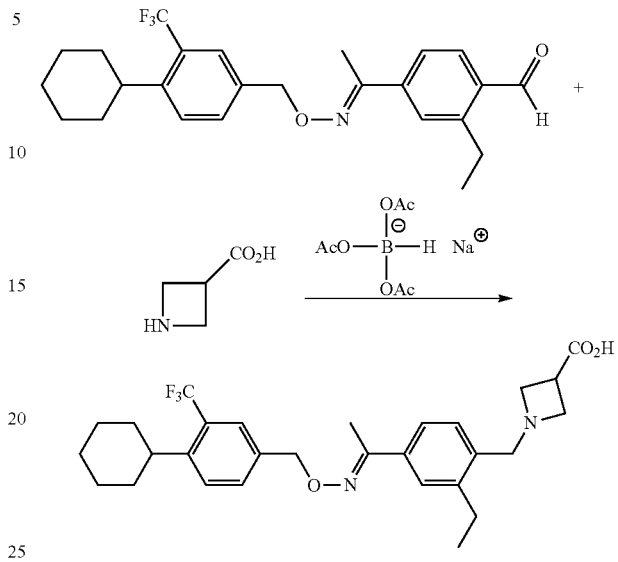

26 g of (E)-4-(1-(((4-cyclohexyl-3-(trifluoromethyl)benzypoxy)imino)ethyl)-2-ethylbenzaldehyde and 8.53 g of azetidine-3-carboxylic acid were suspended in 400 ml of MeOH at 20° C.-25° C. The suspension was stirred at 20° C.-25° C. for 30 minutes. 24.3 g of Sodium triacetoxyborohydride was added in 8 equal portions in 10-15 min intervals. The reaction was finished right after the final portion of the reducing agent was added. The solvent was removed by evaporation and the residue was diluted with 156 ml of water and 312 ml of ethyl acetate. pH of the mixture was adjusted by addition of 75 ml of 2M aqueous NaOH to approx 6 at 20° C.-25° C. The phases were separated and the organic phase was washed with 60 ml of water, dried using MgSO₄ and filtered. To the filtrate was added 170 ml of absolute EtOH, the solution was concentrated to the ½ of the original volume. The mixture was again dried using MgSO₄, filtered and concentrated to amount of 140 g. 170 ml of absolute EtOH absolute was added and the mixture was concentrated to the amount of 140 g. 170 ml of absolute EtOH and 2.4 g of activated charcoal were added and the suspension was agitated for 30 min. The suspension was filtered and the filtrate was concentrated to amount 50 g. To this oily residue, 100 ml of n-heptane was added and the solution was again concentrated to amount 50 g. 100 ml of n-heptane was added and the solution was concentrated to dryness. The formed foam was dried to provide foam that can be crushed to white solid siponimod, 28.22 g (89% of theoretical yield), 98.5% purity (HPLC in).

Example 7: Preparation of 4-cyclohexyl-3-(trifluoromethyl)benzyl methanesulfonate

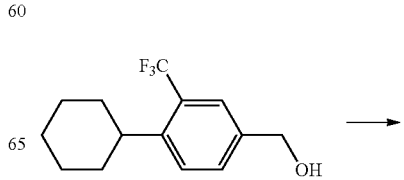

-continued

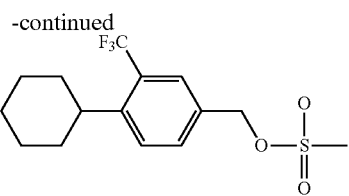

175 g of 4-cyclohexyl-3-(trifluoromethyl)phenyl)methanol was mixed with 875 ml of methyl tert-butyl ether. 140 ml of triethylamine was added. The mixture was cooled to 0° C. 193 g methanesulfonic acid anhydride was mixed with 175 ml of acetonitrile. The temperature of the mixture was set to 25-30° C. The solution of methanesulfonic acid anhydride was added to the mixture of 4-cyclohexyl-3-(trifluoromethyl)phenyl)methanol at temperature 0-5° C. in the course of 50 minutes. Resulting mixture was stirred at 0-5° C. for 30 minutes.

To the reaction mixture, a mixture of 87 g of 36% HCl in 788 g of water was added. The temperature of the mixture was set to 20-25° C. Mixture was stirred for 5 minutes at 20-25° C. and then layers were separated. Organic phase was mixed with 750 ml water and stirred for 5 min and then separated. Operation was performed twice. Organic phase was treated with 20 g of anhydrous $MgSO_4$ and stirred for 10 minutes. Then suspension of 5.25 g active charcoal with 25 ml MTBE was poured into the reaction mixture and it was stirred for another 10 minutes. The mixture was filtrated off and filtrated charcoal was washed with 2×100 ml methyl tert-butyl ether. Methyl tert-butyl ether was distilled off at temperature (20 to 40) ° C. under vacuo until Methyl tert-butyl ether fraction was removed. Mixture was then diluted with 500 ml of n-heptane. Mixture was heated to 70° C. to obtain clear solution. Mixture was cooled to 65° C. Mixture was stirred for another 45 min to start the crystallization.

Mixture was then cooled to 5° C. in the course of 1 hour. The mixture was filtrated off and the filtrated mass was washed with 2×100 ml n-heptane and dried at 65° C., under vacuum and nitrogen atmosphere. The solid 4-cyclohexyl-3-(trifluoromethyl)benzyl methanesulfonate was obtained in yield 94% of the theoretical yield and in purity 99.5% (HPLC IN). The XRPD pattern of obtained solid corresponds to XRPD pattern depicted in FIG. 3, melting point of obtained solid: 90° C. The structure of obtained compound was confirmed by NMR.

Example 8: (E)-1-(3-ethyl-4-(hydroxymethyl)phenyl)ethan-1-one oxime

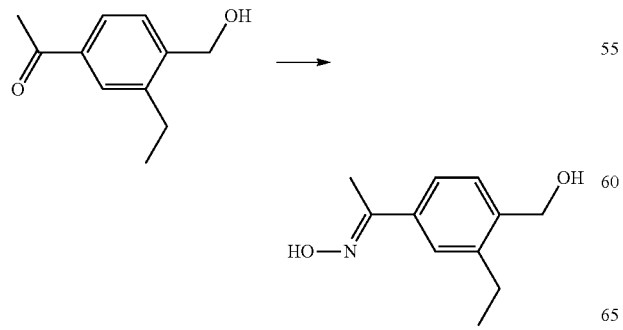

160 g of 1-(3-ethyl-4-(hydroxymethyl)phenyl)ethan-1-one were mixed with 300 ml of methanol at room temperature.

66.8 g hydroxylamine hydrochloride was mixed with 500 ml methanol. The temperature of the mixture was set to 28° C. Clear solution was obtained in about 20 minutes.

To the mixture of 1-(3-ethyl-4-(hydroxymethyl)phenyl)ethan-1-one in methanol 77.4 g of sodium acetate was added. Mixture was cooled to 0° C. Solution of hydroxylamine hydrochloride in methanol was added to the mixture at temperature (0 to 5) ° C. in the course of 20 minutes. Mixture was then stirred for another 1.5 hour at 0-5° C. Mixture was heated to 30° C. and stirred for another 3 hours. After reaction was completed 1600 ml of water was added dropwise into the mixture. The mixture was cooled to 0° C. in the course of 2 hours and stirred for another 1 hour. The mixture was filtered off and obtained solid (E)-1-(3-ethyl-4-(hydroxymethyl)phenyl)ethan-1-one oxime was washed with 400 ml of water. Crystals were blown on filter for 1 hour, dried at 60° C., under vacuum and nitrogen atmosphere. Solid product was obtained in the yield of 92% of the theoretical yield and 99.7% purity (UPLC). Melting point of the product was 102° C.

Example 9: (E)-1-(3-ethyl-4-(hydroxymethyl)phenyl)ethan-1-one O-(4-cyclohexyl-3-(trifluoromethyl)benzyl) oxime

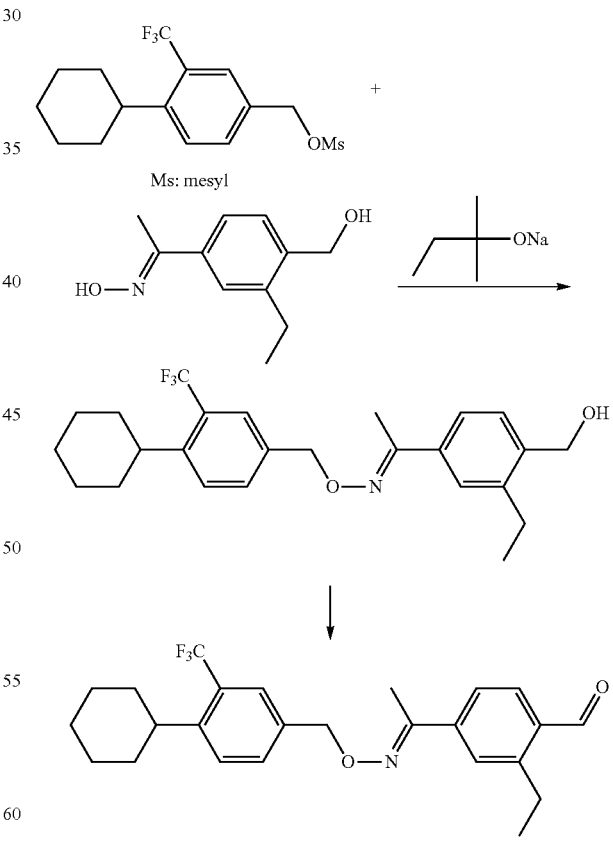

10 g of (E)-1-(3-ethyl-4-(hydroxymethyl)phenyl)ethan-1-one oxime was dissolved in 75 ml of N,N-dimethylformamide and 7 ml of 2-butanol. 6 g of sodium tert-pentoxide in 70 ml of N,N-dimethylformamide was added to reaction mixture. Mixture was stirred for 30 minutes. 17.5 g of 4-cyclohexyl-3-(trifluoromethyl)benzyl methanesulfonate in 200 ml of N,N-dimethylformamide was added dropwise in the course of 25 min and the mixture was stirred for 45 minutes. 170 g of water was added. The mixture warmed by the quench was allowed to cool down to room temperature (20-25° C.) and was extracted with 160 g of n-heptane. The heptane phase was then 2× washed with 150 g of mixture (96 g of N,N-dimethylformamide and 54 g water).

The mixture of (E)-1-(3-ethyl-4-(hydroxymethyl)phenypethan-1-one O-(4-cyclohexyl-3-(trifluoromethyl)benzyl) oxime in heptane was mixed with 200 g of acetonitrile and the phases were separated. The acetonitrile phase was 3× washed with 85 g of n-heptane.

Combined heptane phases were mixed with 85 g of acetonitrile. The phases were separated. Acetonitrile phases were combined. To obtained mixture of (E)-1-(3-ethyl-4-(hydroxymethyl)phenyl)ethan-1-one O-(4-cyclohexyl-3-(trifluoromethyl)benzyl) oxime in acetonitrile 414 mg of CuI, 373 mg of 2,2'-bypiridine, 373 mg of TEMPO and 0.373 ml of N-methylimidazole were added. The mixture was stirred for 2 hours with ambient air being introduced (using gentle evacuation of the flask) under the surface of the reaction mixture. 280 g of water were added dropwise to the mixture. The formed suspension was stirred for 1 hour, isolated by filtration, and isolated solid was washed with 50 ml of mixture acetonitrile/water (1:1). Crystals were blown with air on filter for 1 hour. (E)-1-(3-ethyl-4-(hydroxymethyl)phenyl)ethan-1-one O-(4-cyclohexyl-3-(trifluoromethyl)benzyl) oxime was obtained in yield 78% of the theoretical yield, in purity 99.6% (UPLC). Melting point of obtained solid: 80° C.

XRPD pattern of obtained solid corresponds to XRPD pattern depicted in FIG. 4.

Example 10: Purification of (E)-1-(3-ethyl-4-(hydroxymethyl)phenyl)ethan-1-one O-(4-cyclohexyl-3-(trifluoromethyl)benzyl) oxime 17.5 g of (E)-1-(3-ethyl-4-(hydroxymethyl)phenypethan-1-one O-(4-cyclohexyl-3-(trifluoromethyl)benzyl) oxime were suspended in a mixture of 262.5 g of acetonitrile and 35 g of water and dissolved at 44° C. The mixture was cooled down to 15° C. in the course of 2 hours, stirred for 1 hour at 15° C. isolated by filtration, and isolated solid was washed with 50 ml of mixture acetonitrile/water (1:1). Crystals were blown with air on filter for 1 hour. (E)-1-(3-ethyl-4-(hydroxymethyl)phenypethan-1-one O-(4-cyclohexyl-3-(trifluoromethyl)benzyl) oxime was obtained in yield 70% of the theoretical yield, in purity 99.8% (UPLC). XRPD pattern of obtained solid corresponds to XRPD pattern depicted in FIG. 4.

Example 11: Siponimod

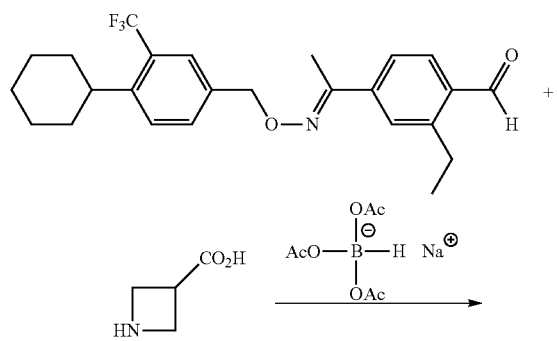

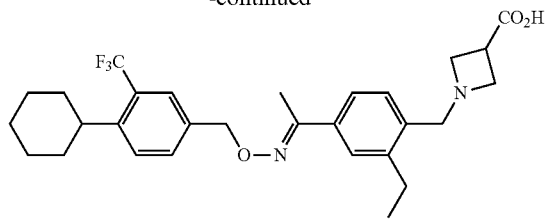

26 g of (E)-4-(1-(((4-cyclohexyl-3-(trifluoromethyl)benzypoxy)imino)ethyl)-2-ethylbenzaldehyde and 8.53 g of azetidine-3-carboxylic acid were suspended in 400 ml of MeOH at 20° C.-25° C. The suspension was stirred at 20° C.-25° C. for 30 minutes. 24.3 g of Sodium triacetoxyborohydride was added in 8 equal portions in 10-15 min intervals. The reaction was finished right after the final portion of the reducing agent was added. The solvent was removed by evaporation and the residue was diluted with 156 ml of water and 312 ml of ethyl acetate. pH of the mixture was adjusted by addition of 75 ml of 2M aqueous NaOH to approx 6 at 20° C.-25° C. The phases were separated and the organic phase was washed with 60 ml of water, dried using MgSO$_4$ and filtered. To the filtrate was added 170 ml of absolute EtOH, the solution was concentrated to the ½ of the original volume. The mixture was again dried using MgSO$_4$, filtered and concentrated to amount of 140 g. 170 ml of absolute EtOH absolute was added and the mixture was concentrated to amount of 140 g. 170 ml of absolute EtOH and 2.4 g of activated charcoal were added and the suspension was agitated for 30 min. The suspension was filtered and the filtrate was concentrated to amount 50 g. To this oily residue, 100 ml of n-heptane was added and the solution was again concentrated to amount 50 g. 100 ml of n-heptane was added and the solution was concentrated to dryness. The formed foam was dried to provide foam that can be crushed to white solid siponimod, 28.22 g (89% of theoretical yield), 98.5% purity (HPLC in).

Example 12: Siponimod

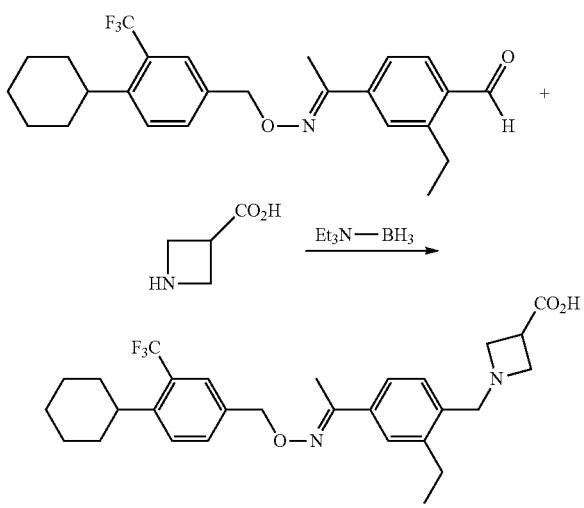

6 g of (E)-4-(1-(((4-cyclohexyl-3-(trifluoromethyl)benzypoxy)imino)ethyl)-2-ethylbenzaldehyde and 2.2 g o azetidine-3-carboxylic acid were suspended in 120 g of MeOH and stirred for 30 minutes. 1.4 ml of Et₃N—BH₃ complex was added dropwise to the suspension during 30 minutes. Reaction mixture was heated to 30° C. after addition and stirred for 3 hours. Reaction mixture was analyzed with respect to compound (Imp). Compound (Imp) cannot be trivially removed from Siponimod.

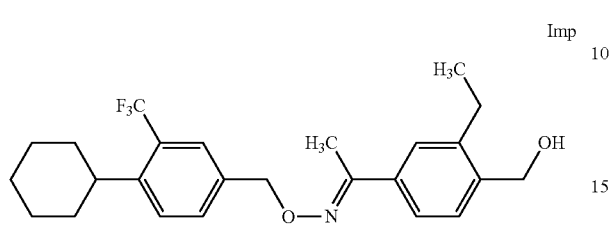

(Imp)

The above procedure was repeated and NaBH(OAc)₃ (disclosed in prior art) was used as the reducing agent.

In the following table the content of compound (Imp), HPLC (IN), in the other words the selectivity of the reduction, for both procedures is stated:

| Reducing agent | Content of compound (IMP) (% HPLC IN) |
|---|---|
| NaBH(OAc)₃ | 3 |
| Et₃N—BH₃ complex | 0.07 |

The amount of the impurity is significantly lower in case Et₃N—BH₃ complex is used as the reducing agent.

The invention claimed is:

1. A process for preparation of Siponimod of formula (I):

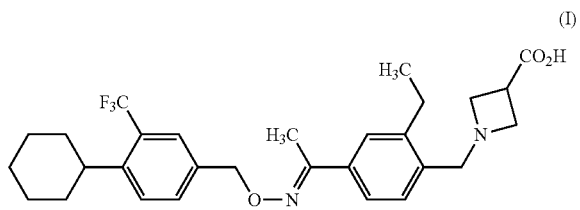 [SMILES: CCc1cc(/C(C)=N/OCc2ccc(C3CCCCC3)c(C(F)(F)F)c2)ccc1CN1CC(C(=O)O)C1]

(I)

or a salt thereof or a solvate thereof, the process comprising:
a) Reacting compound of formula (II) with a compound of formula (III),

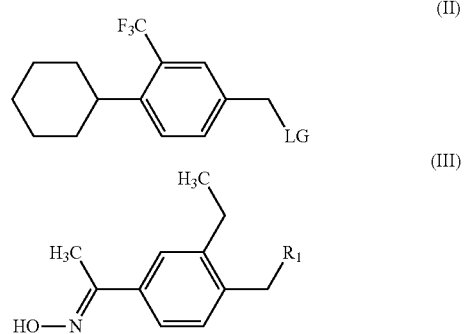

(II)

(III)

wherein LG is a leaving group, R₁ is OH or OProt, and Prot is hydroxyl protective group,
to obtain compound of formula (IV),

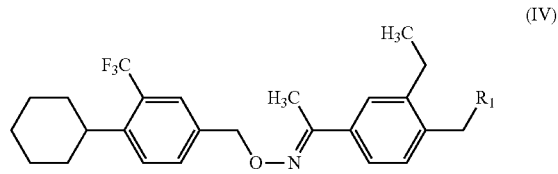

(IV)

wherein R₁ is OH or OProt, and Prot is hydroxyl protective group;
b) Transforming the compound of formula (IV) into Siponimod or a salt thereof or a solvate thereof.

2. The process according to claim 1 wherein LG is a leaving group selected from Cl or Br or I or C₁-C₁₀ alkyl or an aryl sulfonate or a perfluoroalkylsulfonate.

3. The process according to claim 1 wherein the compound of formula (II) is compound of formula (IIb),

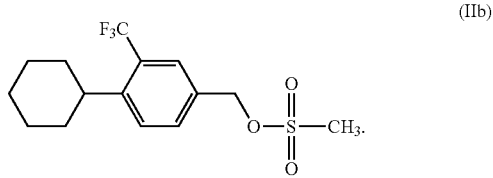 [SMILES: CS(=O)(=O)OCc1ccc(C2CCCCC2)c(C(F)(F)F)c1]

(IIb)

4. The process according to claim 1 wherein the reaction step a) is performed in a solvent selected from N,N-dimethylformamide or a poorly nucleophilic alcohol or 2-methyl-tetrahydrofurane or acetonitrile or dimethylacetamide or a mixture thereof.

5. The process according to claim 4 wherein the reaction step a) is performed in a mixture N,N-dimethylformamide and butan-2-ol.

6. The process according to claim 1 wherein the step a) is performed in a presence of a base.

7. The process according to claim 1, wherein R₁ in the compound of formula (III) is OH and the compound of formula (IV) is a compound of formula (IVa):

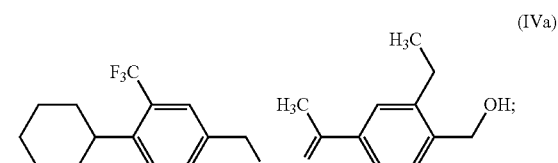

(IVa)

which further comprises:
reacting the compound of formula (IVa) with an oxidating agent to obtain a compound of formula (VII);

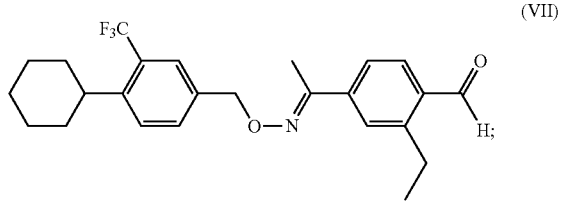

(VII)

and
reacting the compound of formula (VII) with a compound of formula (VIII) in a presence of a reducing agent in a solvent to obtain the compound of formula (I),

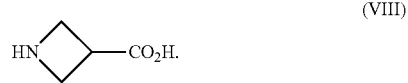

(VIII)

8. The process according to claim 7 wherein the oxidating agent is oxygen.

9. The process according to claim 7 wherein the reducing agent is triethylamine-$BH_3$ ($Et_3N$—$BH_3$) complex.

10. The process according to claim 8 wherein the reducing agent is triethylamine-$BH_3$ ($Et_3N$—$BH_3$) complex.

11. The process according to claim 3, wherein the reaction step a) is performed in a mixture N,N-dimethylformamide and butan-2-ol.

12. The process according to claim 11 wherein the step a) is performed in a presence of a base.

13. The process according to claim 3 wherein the step a) is performed in a presence of a base.

14. The process according to claim 4 wherein the step a) is performed in a presence of a base.

15. The process according to claim 5 wherein the step a) is performed in a presence of a base.

* * * * *